United States Patent
Yang et al.

(10) Patent No.: US 7,794,741 B2
(45) Date of Patent: *Sep. 14, 2010

(54) ENHANCED DELIVERY OF CERTAIN FRAGRANCE COMPONENTS FROM PERSONAL CARE COMPOSITIONS

(75) Inventors: Lin Yang, Woodbridge, CT (US); Prem Chandar, Closter, NJ (US)

(73) Assignee: Conopco, Inc., Englewood Cliffs, NJ (US)

(*) Notice: Subject to any disclaimer, the term of this patent is extended or adjusted under 35 U.S.C. 154(b) by 188 days.

This patent is subject to a terminal disclaimer.

(21) Appl. No.: 11/755,007

(22) Filed: May 30, 2007

(65) Prior Publication Data

US 2008/0299053 A1 Dec. 4, 2008

(51) Int. Cl.
*A61K 8/00* (2006.01)
(52) U.S. Cl. .................................. 424/401; 424/54
(58) Field of Classification Search .............. 424/54, 424/401
See application file for complete search history.

(56) References Cited

U.S. PATENT DOCUMENTS

| | | |
|---|---|---|
| 4,663,159 A | 5/1987 | Brode, II et al. |
| 4,689,217 A | 8/1987 | Restaino et al. |
| 4,690,817 A | 9/1987 | Davis et al. |
| 4,775,715 A | 10/1988 | Beresniewicz et al. |
| 4,978,526 A | 12/1990 | Gesslein et al. |
| 5,135,747 A | 8/1992 | Faryniarz et al. |
| 5,698,183 A | 12/1997 | Langer et al. |
| 5,773,595 A | 6/1998 | Weuthen et al. |
| 5,833,999 A | 11/1998 | Trinh et al. |
| 5,849,310 A | 12/1998 | Trinh et al. |
| 6,086,903 A | 7/2000 | Trinh et al. |
| 6,100,233 A | 8/2000 | Sivik et al. |
| 6,290,978 B2 | 9/2001 | Mak et al. |
| 6,432,907 B1 | 8/2002 | Skold et al. |
| 6,620,410 B1 | 9/2003 | Cho et al. |
| 6,649,177 B2 | 11/2003 | Howard et al. |
| 6,740,317 B1 | 5/2004 | Cho et al. |
| 6,806,249 B2 * | 10/2004 | Yang et al. .................. 512/1 |
| 6,869,977 B1 | 3/2005 | O'Lenick, Jr. et al. |
| 7,176,172 B2 | 2/2007 | Harding et al. |
| 2003/0095990 A1 | 5/2003 | Hua et al. |
| 2003/0206933 A1 | 11/2003 | Schulze zur Wiesche et al. |
| 2003/0211952 A1 | 11/2003 | Erazo-Majewicz et al. |
| 2004/0022818 A1 | 2/2004 | Cho et al. |
| 2004/0110651 A1 | 6/2004 | Harmalker et al. |
| 2004/0156877 A1 | 8/2004 | Tokuyama et al. |
| 2004/0258654 A1 | 12/2004 | Nielsen et al. |
| 2006/0088495 A1 * | 4/2006 | Harichian et al. ........ 424/70.28 |
| 2006/0088496 A1 | 4/2006 | McManus et al. |
| 2006/0089290 A1 | 4/2006 | McManus et al. |
| 2006/0193805 A1 | 8/2006 | Johnson et al. |
| 2007/0048235 A1 | 3/2007 | Harmalker et al. |
| 2007/0053853 A1 | 3/2007 | Hurley et al. |
| 2007/0054820 A1 | 3/2007 | Harichian et al. |

FOREIGN PATENT DOCUMENTS

| | | |
|---|---|---|
| DE | 195 17 048 C1 | 5/1995 |
| EP | 1179339 A2 | 2/2002 |
| EP | 1 552 814 A1 | 8/2003 |
| EP | 1 366 742 A1 | 12/2003 |
| JP | 63068514 | 3/1988 |
| JP | 1249709 | 10/1989 |
| JP | 9012589 | 1/1997 |
| WO | 90/13161 | 11/1990 |
| WO | 00/61066 | 10/2000 |
| WO | 03/037277 A1 | 5/2003 |
| WO | 96/35410 | 2/2006 |
| WO | 2006/045583 A1 | 5/2006 |

OTHER PUBLICATIONS

Dow—Quat 188 Cationic Monomer: Overview, Jun. 30, 2004.
Arch Personal Care Products Brochure—Honeyquat 50 Substantive Honey Derivative, Jan. 2004.
Arch Personal Care Products—In vivo study of moisturizing effects of HoneyQuat 50, Jan. 2004.
Cola Moist 200 Brochure—2004.
Co-Pending Appln.—Applicant: Harichian et al. U.S. Appl. No. 11/557,530, filed Nov. 8, 2006; For: Personal Care Compositions Containing Quaternary Ammonium Trihydroxy Substituted Dipropyl Ether.
Co-Pending Appln.—Applicant: Chandar et al., For: Personal Care Compositions With Enhanced Fragrance Delivery, filed May 30, 2007, U.S. Appl. No. 11/755,009.
Co-Pending Appln.—Applicant: Chandar et al., Filed: May 30, 2007; For: Personal Care Composition With Cocoa Butter And Dihydroxypropyl Ammonium Salts U.S. Appl. No. 11/755,008.
International Search Report PCT/EP/2008/056320, completed Oct. 15, 2008.

* cited by examiner

*Primary Examiner*—Frederick Krass
*Assistant Examiner*—Isaac Shomer
(74) *Attorney, Agent, or Firm*—Milton L. Honig

(57) ABSTRACT

A personal care composition is provided having a fragrance which incorporates limonene, gamma terpinene, ethylene brassylate or combinations thereof in conjunction with a quaternary ammonium salt. The salt has a structure AB, wherein A is a cationic charge component, B is an anionic charge component, and A has one quaternized nitrogen atom, at least two hydroxyl groups and a molecular weight no higher than about 250. The quaternary ammonium salt functions as a scent boosting agent to enhance volatilization of the fragrance components when the personal care composition is first applied to skin or hair of the human body.

3 Claims, No Drawings she# ENHANCED DELIVERY OF CERTAIN FRAGRANCE COMPONENTS FROM PERSONAL CARE COMPOSITIONS

BACKGROUND OF THE INVENTION

1. Field of the Invention

The invention concerns personal care compositions which upon application to a human body surface quickly release certain fragrance components thereby improving aesthetics of these compositions.

2. The Related Art

Perhaps the most significant aesthetic of a personal care product for a consumer is fragrance. It is also important to rapidly deliver the scent.

Many techniques have been reported to manipulate timing and impact of fragrance. Delayed generation has been achieved through encapsulation of scent ingredients. For instance, U.S. Pat. No. 5,135,747 (Faryniarz et al.) reports an unscented malodor counteractant deo perfume mixture encapsulated within a semi-permeable wall material and a quicker releasable non-encapsulated fragrance perfume mixture in a cosmetically acceptable vehicle. Slow release has also been achieved through pro-accords. These chemicals slowly break down releasing an odoriferous component as a degradation fragment. Menthol is the most frequent commercially delivered degradation constituent of pro-accords contained in personal care compositions. Illustrative of this technology is U.S. Pat. No. 6,100,233 (Sivik et al.) employing a β-ketoester pro-accord which transforms to chemically release fragranced alcohols such as linalool, dihydromyrcenol and other alcohols.

Steady release technologies have also been reported. Most prominent are a series of disclosures on enduring perfumes. See U.S. Pat. No. 5,833,999; U.S. Pat. No. 5,849,310 and U.S. Pat. No. 6,086,903 all to Trinh et al. describing personal treatment compositions delivering an enduring perfume that provides a lasting olifactory sensation.

Although technologies are known for delayed release and prolonged perfume generation, none has solved the problem of rapidly releasing a fragrance onto human skin or hair.

SUMMARY OF THE INVENTION

A personal care composition is provided which includes:
(i) from about 0.000001 to about 2% of a fragrance component selected from the group consisting of limonene, gamma terpinene, ethylene brassylate and mixtures thereof;
(ii) from about 0.05% to about 30% by weight of a dihydroxypropyl quaternary ammonium salt of structure AB, wherein A is a cationic charged component of the salt AB, B is an anionic charged component of the salt AB, and A has a single quaternized nitrogen atom, at least two hydroxy groups and a molecular weight no higher than about 250; and
(iii) a cosmetically acceptable carrier.

DETAILED DESCRIPTION OF THE INVENTION

Now it has been found that fragrance components limonene, gamma terpinene and ethylene brassylate can have their volatility enhanced from a personal care composition through use of a scent boosting agent. This agent has been found to be dihydroxypropyl quaternary ammonium salts.

By the term personal care composition is meant any product applied to a human body for improving appearance, cleansing, odor control or general aesthetics. Nonlimiting examples of personal care compositions include leave-on skin lotions and creams, shampoos, conditioners, shower gels, toilet bars, antiperspirants, deodorants, dental products, shave creams, depilatories, lipsticks, foundations, mascara, sunless tanners and sunscreen lotions.

An important material of the present invention is dihydroxypropyl quaternary ammonium salts of structure AB, wherein A is a cationic charged component of the salt AB, and B is an anionic charged component of the salt AB, A has one quaternized nitrogen atom, at least two hydroxyl groups and a molecular weight no higher than about 250 but preferably no higher than about 200, and optimally no higher than 170.

Anionic charged component B may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate. The number and charge of negatively charged component B will be sufficient to neutralize the positive charge of component A.

A preferred embodiment of the quaternary ammonium salts is the dihydroxypropyl tri($C_1$-$C_3$ alkyl or hydroxyalkyl) ammonium salts.

These salts may be obtained in a variety of synthetic procedures, most particularly by hydrolysis of chlorohydroxypropyltri($C_1$-$C_3$ alkyl or hydroxyalkyl) ammonium salts. Ordinarily the $C_1$-$C_3$ alkyl or hydroxyalkyl constituent on the quaternized ammonium group will be methyl, ethyl, n-propyl, isopropyl, hydroxyethyl, hydroxymethyl and mixtures thereof. Particularly preferred is a trimethyl ammonium group known through INCI nomenclature as a "trimonium" group. A most preferred species is 1,2-dihydroxypropyltrimonium chloride, wherein the $C_1$-$C_3$ alkyl is a methyl group.

Amounts of the quaternary ammonium salts may range from about 0.05 to about 30%, preferably from about 0.1 to about 25%, more preferably from about 5 to about 20%, optimally from about 10 to about 15% by weight of the composition.

The fragrance components susceptible of a boost according to the present invention are limonene, gamma terpinene, ethylene brassylate and combinations thereof. Ethylene brassylate is particularly useful as a scent for masking malodor in compositions having essentially no other fragrance component mixtures. Amounts of each of these components may each range from about 0.000001 to about 2%, preferably from about 0.00001 to about 1%, more preferably from about 0.0001 to about 0.5%, and optimally from about 0.001 to about 0.1% by weight of the personal care composition.

Compositions of this invention will also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 $m^2$/s at 25° C. Among the preferred nonvolatile emollients useful in the present compositions are the polydimethyl siloxanes having viscosities from about $1 \times 10^{-5}$ to about $4 \times 10^{-4}$ $m^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
1) Alkyl esters of saturated fatty acids having 10 to 24 carbon atoms. Examples thereof include behenyl neopentanoate, isononyl isonanonoate, isopropyl myristate and octyl stearate.
2) Ether-esters such as fatty acid esters of ethoxylated saturated fatty alcohols.
3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
4) Wax esters such as beeswax, spermaceti wax and tribehenin wax.
5) Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol and cetyl alcohol.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

Surfactants may also be present in compositions of the present invention. Total concentration of the surfactant when present may range from about 0.1 to about 40%, preferably from about 1 to about 20%, optimally from about 1 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionate, $C_8$-$C_{20}$ alkyl ether phosphates, $C_8$-$C_{20}$ sarcosinates and combinations thereof.

Sunscreen actives may also be included in compositions of the present invention. Particularly preferred are such materials as ethylhexyl p-methoxycinnamate (available as Parsol MCX®), Avobenzene (available as Parsol 1789®), octylsalicylate (available as Dermablock OS®), tetraphthalylidene dicamphor sulfonic acid (available as Mexoryl SX®), benzophenone-4 and benzophenone-3 (Oxybenzone). Inorganic sunscreen actives may be employed such as microfine titanium dioxide, zinc oxide, polyethylene and various other polymers. By the term "microfine" is meant particles of average size ranging from about 10 to about 200 nm, preferably from about 20 to about 100 nm. Amounts of the sunscreen agents when present may generally range from 0.1 to 30%, preferably from 2 to 20%, optimally from 4 to 10% by weight of the composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavanoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10%, preferably from 0.01% to 1%, optimally from 0.1 to 0.5% by weight of the composition.

Another type of useful substance can be that of an enzyme such as oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as lipoic acid, kinetin, retinoxytrimethylsilane (available from Clariant Corp. under the Silcare 1 M-75™), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention can also be, optionally, incorporated into a water insoluble substrate for application to the skin such as in the form of a treated wipe.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Dihydroxypropyl Trimonium Chloride | 1.00 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |

TABLE I-continued

| INGREDIENT | WEIGHT % |
| --- | --- |
| PHASE D | |
| Vitamin A Palmitate | 0.10 |
| Bisabolol | 0.01 |
| Vitamin A Acetate | 0.01 |
| Fragrance (20% Limonene and 3% gamma terpinene) | 0.03 |
| Retinol 50C | 0.02 |
| Conjugated Linoleic Acid | 0.50 |

EXAMPLE 2

A water-in-oil topical liquid make-up foundation according to invention is described in Table II below.

TABLE II

| INGREDIENT | WEIGHT % |
| --- | --- |
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance (50% limonene and 10% gamma terpinene) | 0.05 |
| PHASE G | |
| Water | balance |
| Dihydroxypropyl Trimonium Chloride | 3.00 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

EXAMPLE 3

A relatively anhydrous composition incorporating the quat salt and a fragrance mask formed substantially only from ethylene brassylate is reported in Table III.

TABLE III

| INGREDIENT | WEIGHT % |
| --- | --- |
| Cyclomethicone | 60.65 |
| Glycerin | 15.00 |
| Dimethicone | 10.10 |
| Squalane | 6.00 |

TABLE III-continued

| INGREDIENT | WEIGHT % |
| --- | --- |
| Dihydroxypropyltrimonium Chloride | 5.00 |
| Isostearic Acid | 1.90 |
| Ethylene Brassylate | 0.90 |
| Retinyl Palmitate | 0.25 |
| Ceramide 6 | 0.10 |
| Tocopherol | 0.10 |

EXAMPLE 4

An aerosol packaged foaming cleanser with a quat salt and limonene as a major component of the fragrance is outlined in Table IV.

TABLE IV

| INGREDIENT | WEIGHT % |
| --- | --- |
| Sunflower Seed Oil | 10.00 |
| Glycerin | 10.00 |
| Maleated Soybean Oil | 5.00 |
| Silicone Urethane | 1.00 |
| Polyglycero-4 Oleate | 1.00 |
| Sodium C14–16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Dihydroxypropyltrimonium Chloride | 1.00 |
| Fragrance (20% Limonene) | 1.00 |
| Water | Balance |

EXAMPLE 5

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated 1.0 grams of a composition including a quaternary ammonium salt and a fragrance having 20% limonene and 20% gamma terpinene as outlined in Table V below.

TABLE V

| INGREDIENT | WEIGHT % |
| --- | --- |
| Dihydroxypropyltrimonium Chloride | 4.00 |
| Glycerin | 12.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance (20% Limonene and 20% gamma terpinene) | 0.20 |
| Vitamin E Acetate | 0.001 |
| Water | Balance |

EXAMPLE 6

A toilet bar illustrative of the present invention is outlined under Table VI.

TABLE VI

| INGREDIENT | WEIGHT % |
|---|---|
| Sodium Soap (85/15 Tallow/Coconut) | 77.77 |
| Dihydroxypropyltrimonium Chloride | 3.50 |
| Dimethicone | 2.00 |
| Sodium Chloride | 0.77 |
| Titanium Dioxide | 0.40 |
| Ethylene Brassylate | 1.50 |
| Disodium EDTA | 0.02 |
| Sodium Etidronate | 0.02 |
| Fluorescer | 0.024 |
| Water | Balance |

EXAMPLE 7

A shampoo composition useful in the context of the present invention is described in Table VII below.

TABLE VII

| Ingredient | Weight % |
|---|---|
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Glycerin | 12.00 |
| Dihydroxypropyltrimonium Chloride | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance (10% Limonene) | 0.40 |
| Sodium Benzoate | 0.25 |
| Kathon CG ® | 0.0008 |
| Benzyl Alcohol | 0.0225 |
| Water | Balance |

EXAMPLE 8

This Example illustrates an antiperspirant/deodorant formula incorporating the quat salts and ethylene brassylate fragrance mask component according to the present invention.

TABLE VIII

| Ingredient | Weight % |
|---|---|
| Cyclopentasiloxane | 39 |
| Dimethicone | 20 |
| Aluminum Zirconium Trichlorohydrex Glycinate | 15 |
| Dihydroxypropyltrimonium Chloride | 5.0 |
| $C_{18}$–$C_{36}$ Acid Triglyceride | 5.0 |
| Microcrystalline Wax | 3.0 |
| Glycerin | 8.0 |
| Silica | 2.5 |
| Dimethicone Crosspolymer | 1.0 |
| Ethylene Brassylate | 0.5 |
| Disodium EDTA | 0.4 |
| Butylated Hydroxytoluene | 0.3 |
| Citric Acid | 0.3 |

EXAMPLE 9

A series of experiments were conducted to evaluate release and prolonged scent generation of typical components of a perfume mixture. Samples were prepared by mixing 10% of scent boosting agent (dihydroxypropyl quaternary ammonium salt) in water along with 0.05% Deep Moisture perfume oil. This oil is a mixture of components including but not limited to limonene, dihydromyrcenol, benzyl acetate, gamma terpinene, linalool, pinene, isomethyl ionone, and others.

Samples were analyzed by gas chromatography (GC) analysis of headspace gases. In this procedure, the equipment utilized was a solid phase microextraction (SPME) system employing gas chromatography (GC) 6890/mass spectrometry (MS) 5973/flame ionization detector (FID). This equipment measured relative perfume compound abundance in the headspace over the fragrance/boosting agent/water mixture, as well as over the fragrance/water mixture. One gram of fragrance/boosting agent/water mixture was prepared in 20 ml GC headspace sampling vials sealed with caps having septums (from Gerstel, Inc.). The GC column was a HP-5MS column from Agilent (inner diameter 0.25 mm, length 30 m, stationary phase thickness 0.25 um). The GC conditions were as follows: Injector in splitless mode with helium gas as carrier gas. Injection port was heated to 250° C., purge flow to split vent 50 ml/min at zero minutes. Column was in constant flow mode with 1.3 ml/min flow rate. Oven temperature ramp: hold at 75° C. for 2 minutes, then increase oven temperature at a rate of 6° C./min to 100° C., 1.5° C./min to 150° C., 3° C./min to 190° C., 30° C./min to 300° C. and hold for 2 minutes. MS conditions were: solvent delay for 0.5 minutes, scan starting from low mass 35 to high mass 300. Autosampler's conditions were: No incubation (all experiments done in room temperature). SPME fibre was inserted into the sample headspace for a 5 minute extraction and then injected to the injector for a 15 minute desorption.

In the situation of ethylene brassylate, this material was charged at 0.01 g into a 20 g solution of boosting agent/water. The added ethylene brassylate was above the solubility level of this material in the boosting agent/water solution. In the GC headspace analysis for ethylene brassylate, MS conditions were: solvent delay for 0.5 min., SIM mode (selective ion) for 99 and 98 ions. All other conditions were identical to that noted in the previous paragraph.

Results of the experiments are reported in Table IX below.

TABLE IX

| Fragrance Component | Water | 10% GQ |
|---|---|---|
| 1-Butanol, 3-Methyl acetate | 1.00 | 1.09 |
| 2-Buten-1-ol, 3-Methyl acetate | 1.00 | 1.04 |
| Beta pinene | 1.00 | 1.72 |
| Hexyl acetate | 1.00 | 1.41 |
| Limonene | 1.00 | 2.72 |
| 2,6-Dimethyl hept-5-en-1-al | 1.00 | 0.38 |
| Gamma terpinene | 1.00 | 2.15 |
| Dihydromyrcenol | 1.00 | 1.00 |
| 2,4 Dimethyl-3-cyclohexene-1-carbaldehyde | 1.00 | 1.06 |
| Linalool | 1.00 | 0.97 |
| Benzyl acetate | 1.00 | 0.86 |
| Allyl heptoate | 1.00 | 1.23 |
| 2-Tertiobutylcyclohexyl acetate-2 | 1.00 | 1.16 |
| Alpha isomethyl ionone | 1.00 | 0.86 |
| Lily aldehyde | 1.00 | 0.97 |
| Ethylene Brassylate | 1.00 | 2.64 |

GQ = dihydroxypropyl trimonium chloride

Evident from the results in Table IX is that certain fragrance ingredients are particularly boosted into the headspace by the presence of the quat salt. These ingredients are limonene, gamma terpinene and ethylene brassylate.

What is claimed is:

1. A personal care composition comprising:
   (i) from 0.000001 to 2% by weight of a fragrance which is ethylene brassylate;
   (ii) from about 1% to 10% by weight of dihydroxypropyltrimonium chloridea; and
   (iii) a cosmetically acceptable carrier.

2. A composition according to claim 1 wherein ethylene brassylate is present in an amount from about 0.00001 to about 1% by weight of the personal care composition.

3. The composition according to claim 1 wherein ethylene brassylate is present in an amount from about 0.0001 to about 0.5% by weight of the personal care composition.

* * * * *